United States Patent
Sohn et al.

(10) Patent No.: US 6,951,953 B2
(45) Date of Patent: Oct. 4, 2005

(54) TUMOR SELECTIVE AND BIODEGRADABLE POLYPHOSPHAZENE-PLATINUM(II) CONJUGATE ANTITUMOR AGENT, AND PREPARATION METHOD THEREOF

(75) Inventors: Youn Soo Sohn, Seoul (KR); Yong Joo Jun, Seoul (KR); Joo Ik Kim, Gyeonggi-Do (KR)

(73) Assignee: EWHA Womans University, Seoul (KR)

( * ) Notice: Subject to any disclaimer, the term of this patent is extended or adjusted under 35 U.S.C. 154(b) by 0 days.

(21) Appl. No.: 10/752,042

(22) Filed: Jan. 7, 2004

(65) Prior Publication Data

US 2004/0219127 A1 Nov. 4, 2004

(30) Foreign Application Priority Data

Apr. 29, 2003  (KR) .............................. 10-2003-0027130

(51) Int. Cl.$^7$ .......................... C07F 15/00; C08L 85/02; A61K 31/28
(52) U.S. Cl. .......................... 556/17; 556/13; 525/538; 514/492; 424/34; 424/78
(58) Field of Search .................... 556/13, 17; 525/538; 514/492; 424/34, 78, 78.34

(56) References Cited

U.S. PATENT DOCUMENTS

| | | | | | |
|---|---|---|---|---|---|
| 4,151,185 | A | * | 4/1979 | Allcock et al. | 525/340 |
| 5,665,343 | A | * | 9/1997 | Sohn et al. | 424/78.26 |
| 6,392,008 | B1 | * | 5/2002 | Allcock et al. | 528/399 |

OTHER PUBLICATIONS

Song et al., Polymer International, vol. 48, No. 8, pp. 627–629 (1999).*
Song et al., Journal of Controlled Release, vol. 55, No. 2–3, pp. 161–170 (1998).*
Sohn et al., International Journal of Pharmaceutics, vol. 153, No. 1, pp. 79–91 (1997).*
D. Lebwohl et al., "Clinical Development of Platinum Complexes in Cancer Therapy: An Historical Perspective and an Update," European Journal of Cancer, vol. 34, No. 10, pp. 1522–1534, 1998.
E. Wong et al., "Current Status of Platinum–Based Antitumor Drugs," Chem. Rev., vol. 99, pp. 2451–2466, 1999.
L. Seymour et al., "Influence of Molecular Weight on Passive Tumor Accumulation of a Soluble Macromalecular Drug Carrier," European Journal of Cancer, vol. 31A, No. 5, pp. 766–770, 1995.
R. Duncan., "Polymer Conjugates for Tumor Targeting and Intracytoplasmic Delivery. The EPR Effect as a Common Gateway," PSTT, vol. 2, No. 11, pp. 441–449, 1999.

H. Maeda et al., "Vascular Permeability Enhancement in Solid Tumor: Various Factors, Mechanissms Involved and its Implications," International Immunopharmacoclogy, vol. 3, pp. 319–328, 2003.
E. Marecos, "Antibody–Medicated Versus Nontargeted Delivery in a Human Small Cell Lung Carcinoma Model," Bioconjugate Chem., vol. 9, pp. 184–191, 1998.
A. Lundberg et al., "Control of the Cell and Apoptosis," European Journal of Cancer, vol. 35, No. 4, p. 531–539, 1999.
K. Tsuchiya et al., "Tumor–Targeted Chemotherapy with SMANCS in Lipiodol for Renal Cell Carcinoma: Llonger Survival with Larger Size Tumors," Adult Urology, vol. 55, No. 4, pp. 495–500, 2000.
P. Vassey et al., "Phase I Clinical and Pharmacokinetic Study of PK1 [N–(2–Hydroxypropyl)Methacrylamide Copolymer Doxorubicin]: First Member of a New Class of Chemotherapeutic Agents– Drug–Polymer Conjugates," Clinical Cancer Research, vol. 5, pp. 83–94, 1999.
H. Allcock et al., "Synthesis of High Polymeric Alkoxy–and Aryloxyphosphonitriles," Journal of the American Cancer Society, vol. 87, No. 18, pp. 4216–4217, 1965.
Y. Sohn et al., "Synthesis and Properties of Low Molecular Weight Polyphosphazenes," Macromolecules, vol. 28, No. 22, pp. 7566–7568, 1995.
S. Song et al., "A New Class of Biodegradable Thermosensitive Polmers. I. Synthesis and Characterization of PO;Y–(Organophosphazenes) with Methoxy–Poly(Ethylene Glycol) and Amino Acid Esters as Side Groups," Macromolecules, vol. 32, No. 7, pp. 2188–2193, 1999.

* cited by examiner

Primary Examiner—Porfirio Nazario-Gonzalez
(74) Attorney, Agent, or Firm—Morrison & Foerster LLP

(57) ABSTRACT

Disclosed are a new class of a polyphosphazene-platinum (II) conjugate antitumor agent having high tumor tissue selectivity due to its enhanced permeability and retention effect to tumor tissues, and a preparation method thereof:

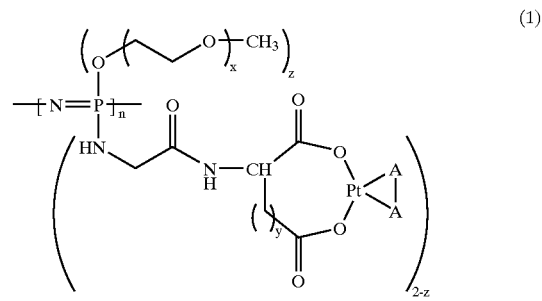

(1)

wherein x represents the number of the ethylene oxide repeating unit and is 7, 12 or 16; y is 0, 1 or 2; z represents molar content of polyethylene glycol in the range of 0.5–1.5; n represents degree of polymerization of polyphosphazene in the range of 30–100; and A-A represents a diamine.

10 Claims, No Drawings

TUMOR SELECTIVE AND BIODEGRADABLE POLYPHOSPHAZENE-PLATINUM(II) CONJUGATE ANTITUMOR AGENT, AND PREPARATION METHOD THEREOF

BACKGROUND OF THE INVENTION

1. Field of the Invention

The present invention relates to a tumor selective and biodegradable polyphosphazene-platinum(II) conjugate antitumor agent and a preparation method thereof.

2. Description of the Prior Art

The platinum(II) antitumor agent such as cisplatin or carboplatin is one of the most widely used antitumor agents in the world. In particular, it has been is known that cisplatin shows superior antitumor activities against testicular cancer, ovarian cancer, bladder cancer, etc.

Cisplatin, which is the first-generation platinum group antitumor agent having a simple structure, is disadvantageous in that it has been restricted in use for cancer treatment due to its severe adverse effects on kidney, bone marrow and nervous system as well as its acquired resistence in long term use and low solubility in water, etc. (D. Lebwohl, R. Canetta, *Eur. J. Cancer,* 34, 1522 (1998)).

Accordingly, a great deal of researches for the development of new platinum complexes having lower toxicity and higher solubility in water, as well as being capable of overcoming drug-resistance, have been actively performed worldwide. As a result, carboplatin was developed as a second-generation platinum group antitumor agent and presently used in clinic (E. Wong, C. M. Giandomenico, *Chem, Rev.,* 99, 2451 (1999)). In carboplatin, chloride anions were replaced with a dicarboxylate anion, thereby to improve solubility in water and to reduce toxicity.

However, in spite that toxicity has been reduced, carboplatin shows stronger adverse effect on bone marrow with lower and narrower spectrum of antitumor activity compared with cisplatin. Therefore, it has been used only for a patient of ovarian cancer or lung cancer having a kidney dysfunction. Therefore, development of a next generation antitumor agent having low toxicity, high solubility in water, high tumor selectivity and the like are urgently required.

In the meantime, since the discovery that polymers with appropriate molecular weights show preferentially enhanced permeability and retention in solid tumor tissues (L. W. Seymour, Y. Miyamoto, H. Maeda, M. Brereton, J. Strohalem, K. Ulbrich and R. Duncan, *Eur. J. Cancer,* 31A, 766 (1995).), a great deal of researches have been performed worldwide for development of new polymeric materials showing high tumor selectivity.

Two probable reasons why polymers with appropriate molecular weights show high tumor tissue selectivity are as follows:

The first one is that although a macromolecule such as a polymeric nano-particle can not permeate through the blood vessel walls in the normal tissues composed of regularly arrayed cells, it can permeate through the blood vessel walls in tumor tissues due to the coarse blood vessel walls of the tumor tissues as well as to the high vascular pressure in tumor tissues. The second one is that there is no lymphatic vessel as a discharge path for a biopolymer and polymer structure in tumor tissues. Therefore, in the tumor tissues, it is difficult for the polymer particles permeated therein to be discharged compared with in normal cells (R. Duncan, *Parm. Sci. Technol. Today.,* 2, 441(1999)), and consequently, polymer particles permeated through the blood vessels wall are selectively accumulated in tumor tissues (H. Maeda, J. Fang, T. Inutsuka, *Inter Immun* 3, 319(2003)), yielding high selectivity of polymers to the tumor tissues.

The degree of such enhanced permeability and retention (EPR) effect of polymer particles closely depends on their residual times within blood and tissues. A polymer having a long blood circulation time can be regarded as a polymer having potential tumor tissue selectivity due to its enhanced permeability and retention effect. And it has been known that a long residual time of the polymer particles in tumor tissues is an essential condition for tumor tissue selectivity (E. Marecos, R. Weissleder, *Bioconjugate Chem.* 9, 184 (1998)). The above-described effects have been known only for some specific polymers, which illustrated from the recent clinical trials on human tumor tissues that such polymers can have high selectivity for tumor tissues, and therefore, can be applied to a selective antitumor agent.

Accordingly, many researches for the development of drug delivery systems using specific bio-affinitive polymer materials have been performed actively around the world (A. S. Lundberg and R. A. Weinberg, *Eur, J, Cancer,* 35, 531–539(1999)). A few examples of such attempts include SMANCS (neocarzinostatin bound to styrene-maleic anhydride copolymer) developed in Japan (K. Tsuchia, H. Maeda, *Urology,* 55, 495(2000)), and a conjugate of N-(2-hydroxypropyl)methacrylamide (HPMA) and doxorubicin (P. A. Vasey, C. Twelves, *Clin. Cancer Res.,* 5, 83 (1999)). The former SMANCS was recently approved in Japan, but are not widely used, and the latter has not been approved yet for clinical use. The main disadvantages of such conventional organic polymers are concerned with their biodegradability and low selectivity for tumor tissues.

Polyphosphazene is a new class of inorganic/organic hybrid polymer, which was first synthesized by Allcock Group in the United States (H. R. Allcock and R. L. Kugel, *J. Am. Chem. Soc.,* 87, 4216(1965)). Polyphosphazene is a linear polymer in which its polymer backbone consists of phosphorus and nitrogen atoms alternately and organic substituents are linked to the phosphorus atoms as side groups, and exhibits a variety of different physical properties depending on the molecular structure of the side chains. Even though polyphosphazenes have good physical properties that organic polymers do not have, they could not have been widely used due to their expensiveness, and only used for limited purpose. In particular, polyphosphazenes could not be developed as drug delivery systems because of their high molecular weight (Mw>$10^6$ daltons) when prepared by the conventional method while polymers as a drug delivery material are required to have maximum molecular weight of 50,000–70,000 daltons for biocompatibility.

The present inventors discovered that the molecular weight of polyphosphazenes can be controlled by the amount of aluminum chloride used as a catalyst for the thermal polymerization reaction of the starting hexachlorocyclotriphosphazene ($N_3P_3Cl_6$) to produce poly(dichlorophosphazene), $(NPCl_2)_n$ (Youn Soo Sohn, et al., *Macromolecules,* 28, 7566 (1995)). Based on this discovery, the present inventors have performed researches for developing various new drug delivery materials. In particular, the present inventors recently discovered that water-solubility and biodegradability of polyphosphazenes can be controlled by introducing a hydrophilic poly(ethylene glycol) and a lipophilic amino acid into the polyphosphazene backbone by nucleophilic substitution of poly(dichlorophosphazene)

(Youn Soo Sohn, et al. *Macromolecules*, 32, 2188 (1999)). The present inventors have also performed researches for applying the same for various purposes.

SUMMARY OF THE INVENTION

It is an object of the present invention to provide a polymer drug delivery material having high tumor tissue selectivity due to its enhanced permeability and retention effect to tumor tissues.

It is another object of the present invention to provide a polymeric platinum conjugate antitumor agent capable of having high tumor selectivity and antitumor activity in which a platinum complex antitumor agent is chemically linked to the above polymer drug delivery material, and to provide a preparation method thereof.

The above and other objects of the invention, as embodied and broadly described herein, can be achieved by conjugating a platinum complex antitumor agent to a nano-sized polyphosphazene (10–100 nm), thereby to provide a new class of polyphosphazene-platinum(II) conjugate antitumor agent having high tumor selectivity.

The foregoing and other objects, features, aspects and advantages of the present invention will become more apparent from the following detailed description of the invention.

DETAILED DESCRIPTION OF THE PREFERRED EMBODIMENT

According to the present invention, a new polymeric antitumor agent having high tumor selectivity, in which a platinum complex antitumor agent is conjugated to a nano-sized polyphosphazene (10–100 nm), is provided. In more detail, a polyphosphazene-platinum(II) conjugate having high tumor selectivity and antitumor activities, in which a platinum(II) complex is chemically linked to a water-soluble nano-sized polyphosphazene obtained by substituting chloride ions of polydichlorophosphazene (Youn Soo Sohn, et al. *Macromolecules*, 28, 7566 (1995)) with poly(ethylene glycol) and dipeptide ethyl esters, is provided.

Therefore, the present invention relates to a new class of polyphosphazene-platinum(II) conjugate antitumor agent having excellent permeability and retention effect to tumor tissues, as well as showing outstanding anticancer activity, in which the molar ratio of the hydrophilic poly(ethylene glycol) and the hydrophobic dipeptide ethyl ester side groups is optimized in a polyphosphazene and a platinum complex antitumor agent is conjugated to this polyphosphazene derivative using the hydrolyzed dipeptide as a spacer, and to a preparation method thereof.

In particular, the present invention relates to a tumor selective and biodegradable polyphosphazene-platinum(II) conjugate antitumor agent represented by the following chemical formula (1), and to a preparation method thereof:

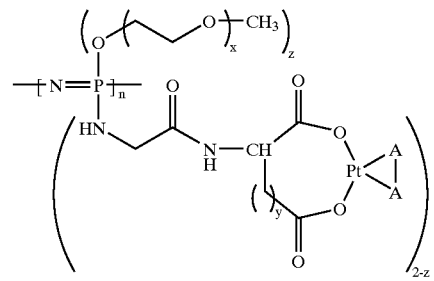

wherein x represents the number of ethylene oxide repeating unit in poly(ethylene glycol) and is 7, 12 or 16; y is an integer of 0 to 2; z represents mole fraction of poly(ethylene glycol) in the range of 0.5–1.5; n represents the degree of polymerization of polyphosphazene in the range of 30–100; and A-A represents a diamine selected from the group consisting of trans($\pm$)-1,2-diaminocyclohexane, 2,2-dimethyl-1,3-propanediamine and ethylenediamine.

Polyphosphazene-platinum(II) conjugate represented by the above chemical formula (1) has a hydrodynamic volume with a diameter of 10–100 nm in an aqueous solution.

The present invention also relates to the use of the polyphosphazene-platinum(II) conjugate represented by chemical formula (1) for treating a tumor.

The polymeric polyphosphazene-platinum(II) conjugate represented by chemical formula (1) can be prepared as follows:

The whole reaction process for preparing the polymeric polyphosphazene-platinum(II) conjugate of the present invention are preferably carried out in inert atmosphere using Schlenk lines and glove box in order to prevent moisture from the reaction system and all solvents used also are thoroughly dried prior to use to eliminate any trace of moisture.

In the first step, phosphazene trimer represented by chemical formula (2) is thermally polymerized according to the known method (Youn Soo Sohn, et al., *Macromolecules*, 28, 7566 (1995)), to obtain a linear poly (dichlorophosphazene) having weight averaged molecular weight of $10^4$–$10^5$ and represented by chemical formula (3):

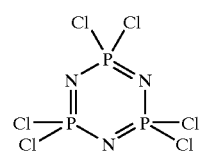

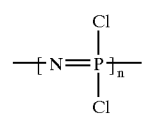

wherein n represents the degree of polymerization in the range of 30–100.

The above thermal polymerization reaction is carried out by mixing hexachlorocyclotriphosphazene $(N=PCl_2)_3$ represented by chemical formula (2) and 3–10 wt. % of aluminum chloride ($AlCl_3$) in a pyrex reaction tube, which is then sealed and subjected to melt reaction at 230–250° C. for 3–5 hours in a reaction oven, in which the reaction tube is rotated at 10–20 rpm.

In the meantime, poly(ethylene glycol) monomethyl ether represented by chemical formula (4) vacuum-dried in an oil bath at 70–80° C. for 1–2 days is reacted with 1.5 equivalents of metallic sodium in a solvent such as tetrahydrofuran (THF), benzene or toluene to obtain a sodium salt of poly(ethylene glycol represented) of chemical formula (5):

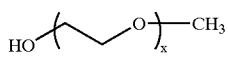
(4)

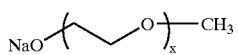
(5)

wherein x represents the number of $(CH_2CH_2O)$ repeating of 7, 12 or 16.

In the second step, a solution of the sodium salt represented by chemical formula (5) is added to a solution of poly(dichlorophosphazene) represented by chemical formula (3) in the presence of triethylamine at the temperature range of from −60° C. to −78° C., and then the resulting solution mixture is stirred at room temperature for 15–20 hours. The amount of the sodium salt of poly(ethylene glycol) used is 0.5–1.5 equivalent per mole of poly (dichlorophosphazene).

In the third step, the partially substituted product from the above reaction is reacted in chloroform at room temperature with 1.5–2.0 equivalents of dipeptide ethylester represented by chemical formula (6) and 3.0 equivalents of triethylamine per one chlorine atom remained unsubstituted to obtain a polyphosphazene derivative represented by chemical formula (7).

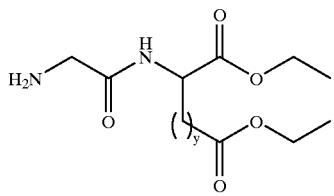
(6)

wherein y is 0, 1 or 2. The dipeptide ethylester represented by the above chemical formula (6) is glycylaminomalonate when y is 0, glycylaspartate when y is 1, and glycylglutamate when y is 2.

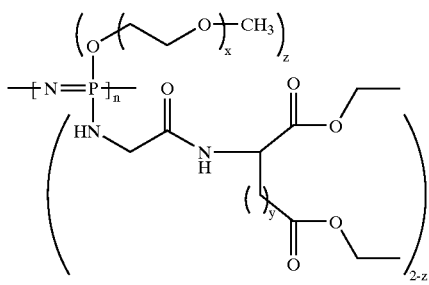
(7)

wherein n, x, y and z are the same as defined in chemical formula (1).

In the fourth step, the dipeptide ethyl ester of the polyphosphazene derivative represented by chemical formula (7) is hydrolyzed using an alkali in methanol to obtain a metallic salt of the dipeptide. It is preferable to use barium hydroxide or sodium hydroxide as an alkali in an amount of 2.4–3.0 equivalents per mole of the dipeptide present in the polyphosphazene derivative represented by chemical formula (7).

Finally, the metallic salt of the dipeptide obtained above is reacted in water in the absence of light with a platinum complex represented by the following chemical formula (8) in an amount of 1.2–1.5 moles per mole of the dipeptide, to obtain the polyphosphazene-platinum(II) conjugate according to the present invention represented by chemical formula (1).

(A-A)PtL   (8)

wherein A-A is the same as defined in chemical formula (1), and L is one or two anionic ligands preferably selected from sulfate ion $(SO_4^{2-})$ and nitrate ion $(NO_3^-)$.

The preparation method of the polyphosphazene-platinum (II) conjugate as described above can be shown in the following reaction scheme (1).

Reaction Scheme (1):

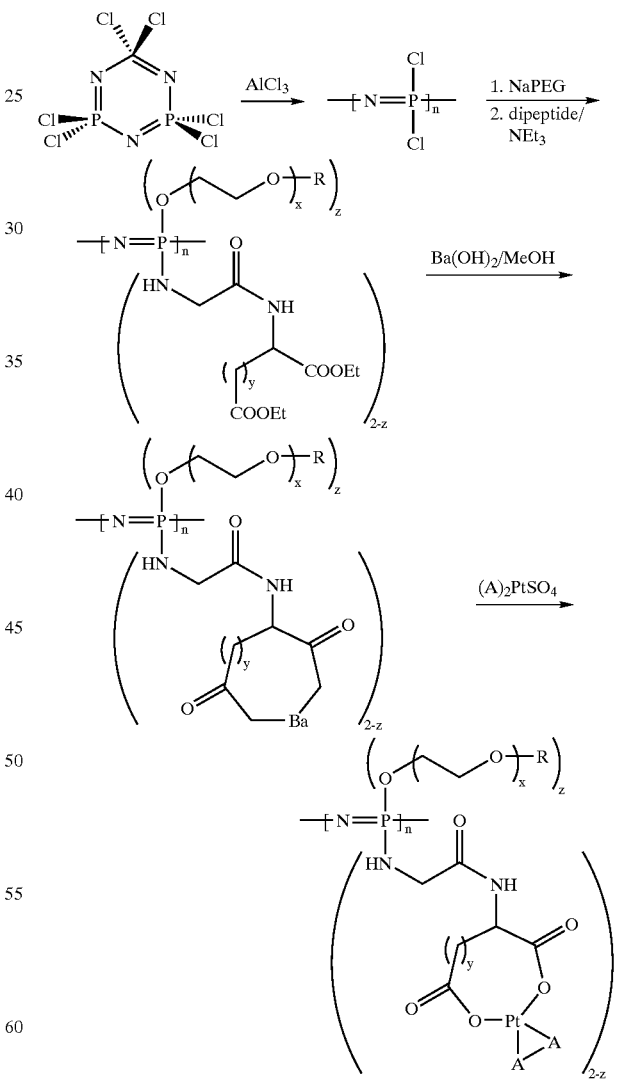

The following reaction scheme (2) shows a reaction process in which sodium hydroxide, instead of barium hydroxide, is used in hydrolysis of the dipeptide ethylester.

Reaction Scheme (2):

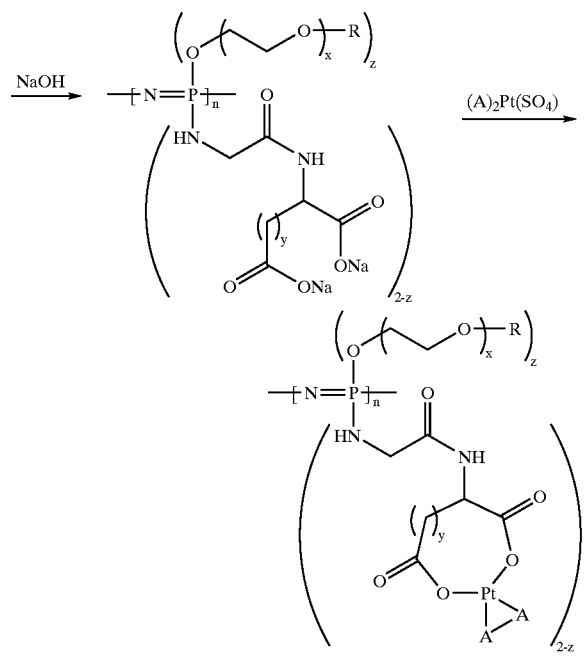

In the above reaction schemes (1) and (2), n, x, y, z and A-A are the same as defined in chemical formula (1).

EXAMPLES

Hereinafter, the present invention will be described in more detail with reference to the following examples and embodiments, but the present invention is not limited thereto.

In the following examples, elemental analysis of carbon, hydrogen and nitrogen for the compound of the present invention was performed using Perkin-Elmer C, H and N analyzer. Hydrogen nuclear magnetic resonance spectra were measured using Bruker DPX-250 NMR spectrometer and platinum nuclear magnetic resonance spectra were measured using Varian Gemini-300 NMR spectrometer. Infrared absorption spectra were measured using Nicolet Impact 400 RF-IR spectrometer.

Example 1

Preparation of poly{[methoxy poly(ethylene glycol) 350][glycylglutamato-trans-(±)-1,2-diaminocyclohexaneplatinum(II)]phosphazene}, {NP(MPEG350)$_{1.5}$[(GlyGlu)Pt(dach)]$_{0.5}$}$_n$ Methoxy poly(ethylene glycol) with average molecular weight of 350 (8.80 g, 25.9 mmol) and a piece of sodium (0.7 g, 30.0 mmol) were added into a dried tetrahydrofuran, and the resulting mixture was refluxed for 24 hours under an argon atmosphere to obtain sodium salt of methoxy poly (ethylene glycol).

Poly(dichlorophosphazene) (2.00 g, 17.2 mmol) prepared using 10% AlCl$_3$ as catalyst was dissolved in dried tetrahydrofuran (80 ml), and to the resulting solution in a dry ice-acetone bath (−78° C.), was added the above-mentioned solution of the sodium salt of methoxy poly(ethylene glycol) dropwise for 30 minutes. After 30 minutes, the dry ice-acetone bath was removed and the reaction solution was further stirred at room temperature for 8 hours. To this solution was added a solution of triethylamine (8.4 g, 84.4 mmol) and glycylglutamic acid diethyl ester (4.5 g, 15 mmol) in chloroform (100 ml). The resulting solution mixture was stirred at room temperature for 12 hours, and then further reacted at 70° C. for 48 hours.

After the precipitate (Et$_3$N.HCl/NaCl) formed in the reaction mixture was removed by filtering, the filtrate was concentrated under a reduced pressure. The concentrate was dissolved in tetrahydrofuran and then excess amount of ether or hexane was added thereto in order to induce precipitation. After repeating this process twice, the precipitate was dissolved in a small amount of water (100 ml), dialyzed for 18 hours using a dialysis membrane (MWCO: 3500), and then freeze dried to obtain the oily polyphosphazene derivative [NP(MPEG)$_{1.5}$(GlyGluEt$_2$)$_{0.5}$] (yield: 80%).

The polyphosphazene derivative obtained above (2.00 g, 3 mmol) was dissolved in methanol (50 ml), to which a methanol solution of Ba(OH)$_2$.8H$_2$O(0.79 g, 2.5 mmol) was added, thereby to perform hydrolysis. After the reaction mixture was concentrated under a reduced pressure, methanol and excess amount of ether were added to induce precipitation of the barium salt of the polyphosphazene derivative. This barium salt was dissolved in a small amount of water (50 ml), to which a solution of trans(±)-1,2-diaminocyclohexane platinum(II) sulfate, Pt(dach)SO$_4$, (1.1 g, 2.5 mmol) in water (30 ml) was then added dropwise at 0° C. for 10 minutes while maintaining pH 7. After the resulting solution was stirred for 4–6 hours, precipitate (BaSO$_4$) was removed by vacuum filtering. After the filtrate was dialyzed in distilled water for 8 hours using a dialysis membrane (MWCO: 3500), it was freeze-dried for one day to obtain 1.90 g (yield: 74%) of the desired final product of the polyphosphazene-platinum(II) conjugate [NP ((OCH$_2$CH$_2$)$_7$OCH$_3$)$_{1.5}$—(NHCH$_2$CONHCH(COO) CH$_2$CH$_2$COO(Pt(dach))$_{0.5}$].

Composition: C$_{29}$H$_{58}$N$_3$O$_{14}$PPt

Elemental analysis data: C(40.48), H(8.18), N(6.33), Pt(13.20)

Theoretical value: C(41.16), H(7.08), N(6.07), Pt(12.80)

H-NMR spectra:

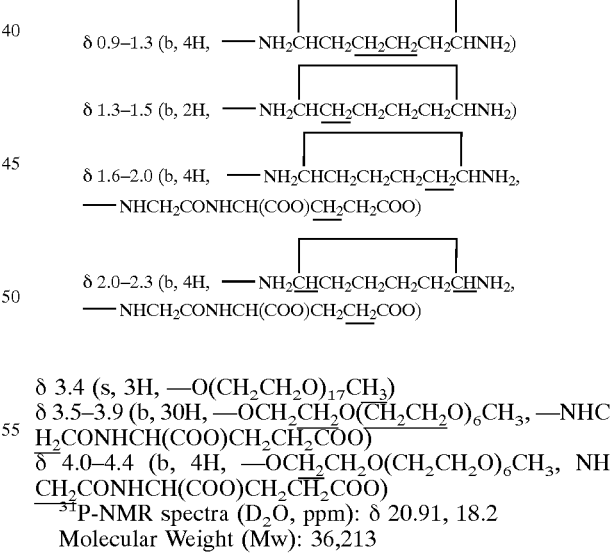

δ 0.9–1.3 (b, 4H, —NH$_2$CHCH$_2$CH$_2$CH$_2$CH$_2$CHNH$_2$)

δ 1.3–1.5 (b, 2H, —NH$_2$CHCH$_2$CH$_2$CH$_2$CH$_2$CHNH$_2$)

δ 1.6–2.0 (b, 4H, —NH$_2$CHCH$_2$CH$_2$CH$_2$CH$_2$CHNH$_2$, —NHCH$_2$CONHCH(COO)CH$_2$CH$_2$COO)

δ 2.0–2.3 (b, 4H, —NH$_2$CHCH$_2$CH$_2$CH$_2$CH$_2$CHNH$_2$, —NHCH$_2$CONHCH(COO)CH$_2$CH$_2$COO)

δ 3.4 (s, 3H, —O(CH$_2$CH$_2$O)$_{17}$CH$_3$)
δ 3.5–3.9 (b, 30H, —OCH$_2$CH$_2$O(CH$_2$CH$_2$O)$_6$CH$_3$, —NHCH$_2$CONHCH(COO)CH$_2$CH$_2$COO)
δ 4.0–4.4 (b, 4H, —OCH$_2$CH$_2$O(CH$_2$CH$_2$O)$_6$CH$_3$, NHCH$_2$CONHCH(COO)CH$_2$CH$_2$COO)
$^{31}$P-NMR spectra (D$_2$O, ppm): δ 20.91, 18.2

Molecular Weight (Mw): 36,213

Example 2

Preparation of poly{[methoxy poly(ethylene glycol) 350][glycylglutamato-trans-(±)-1,2-diaminocyclohexaneplatinum(II)]phosphazene}, {NP(MPEG350)$_{1.2}$[(GlyGlu)Pt(dach)]$_{0.8}$}$_n$ According to the same method as described in Example 1, an ethyl ester of the polyphosphazene derivative was prepared by using methoxy poly(ethylene glycol) having molecular weight of 350 (7.24 g, 25.3 mmol), a piece of sodium metal (0.69 g, 30 mmol), poly (dichlorophosphazene) (10% AlCl$_3$, 2.00 g, 17.2 mmol), triethylamine (18.86 g, 186.3 mmol) and glycylglutamic acid ethyl ester (6.0 g, 20.33 mmol).

After the ethyl ester of the polyphosphazene derivative (2.0 g, 2:97 mmol) was hydrolyzed with NaOH (0.2 g, 5.0 mmol), the hydrolyzed product was reacted with Pt(dach)SO$_4$ (1.01 g, 2.5 mmol) according to the method as described in Example 1, to obtain the desired product of polyphosphazene-platinum(II) conjugate in 70% yield.

Composition: $C_{28}H_{54}N_5O_{13}PPt$

Elemental analysis data: C(38.45), H(6.86), N(6.68), Pt(13.4)

Theoretical value: C(39.56), H(6.08), N(6.83), Pt(17.81)

H-NMR spectra (D$_2$O, ppm):

δ 0.9–1.3 (b, 4H, —NH$_2$CHCH$_2$CH$_2$CH$_2$CH$_2$CHNH$_2$)

δ 1.3–1.5 (b, 2H, —NH$_2$CHCH$_2$CH$_2$CH$_2$CH$_2$CHNH$_2$)

δ 1.6–2.0 (b, 4H, —NH$_2$CHCH$_2$CH$_2$CH$_2$CH$_2$CHNH$_2$, —HCH$_2$CONHCH(COO)CH$_2$CH$_2$COO)

δ 2.0–2.3 (b, 4H, —NH$_2$CHCH$_2$CH$_2$CH$_2$CH$_2$CHNH$_2$, —NHCH$_2$CONHCH(COO)CH$_2$CH$_2$COO)

δ 3.4 (s, 3H, —O(CH$_2$CH$_2$O)$_7$CH$_3$)
δ 3.5–3.9 (b, 30H, —OCH$_2$CH$_2$O(CH$_2$CH$_2$O)$_6$CH$_3$, —NHCH$_2$CONHCH(COO)CH$_2$CH$_2$COO)
δ 4.0–4.4 (b, 4H, —OCH$_2$CH$_2$O(CH$_2$CH$_2$O)$_6$CH$_3$, —NHCH$_2$CONHCH(COO)CH$_2$CH$_2$COO)

$^{31}$P-NMR spectra: δ 18.2, 22.3 ppm

Molecular Weight (Mw): 35,213

Example 3

Preparation of poly{[methoxy poly(ethylene glycol) 350][glycylglutamato-trans-(±)-1,2-diaminocyclohexaneplatinum(II)]phosphazene}, {NP(MPEG350)$_{1.0}$[(GlyGlu)Pt(dach)]$_{1.0}$}$_n$ According to the same method as described in Example 1, the desired product of the title polyphosphazene-platinum (II) conjugate was prepared by using methoxy poly(ethylene glycol) having molecular weight of 350 (6.35 g, 17.3 mmol), a piece of sodium metal (1.0 g, 25 mmol), poly (dichlorophosphazene) (10% AlCl$_3$, 2.00 g, 17.2 mmol), triethylamine (18.86 g, 186.3 mmol), glycylglutamic acid ethyl ester (6.10 g, 20.8 mmol), Ba(OH)$_2$.8H$_2$O(1.11 g, 3.5 mmol) and Pt(dach)SO$_4$ (1.42 g, 3.5 mmol) in 78.0% yield.

Composition: $C_{29}H_{55}N_5O_{13}PPt$

Elemental analysis data: C(37.58), H(6.08), N(7.83), Pt(21.1)

Theoretical Value: C(38.37), H(6.11), N(7.71), Pt(21.49)

H-NMR spectra (D$_2$O, ppm):

δ 0.9–1.3 (b, 4H, —NH$_2$CHCH$_2$CH$_2$CH$_2$CH$_2$CHNH$_2$)

δ 1.3–1.5 (b, 2H, —NH$_2$CHCH$_2$CH$_2$CH$_2$CH$_2$CHNH$_2$)

δ 1.6–2.0 (b, 4H, —NH$_2$CHCH$_2$CH$_2$CH$_2$CH$_2$CHNH$_2$, —HCH$_2$CONHCH(COO)CH$_2$CH$_2$COO)

δ 2.0–2.3 (b, 4H, —NH$_2$CHCH$_2$CH$_2$CH$_2$CH$_2$CHNH$_2$, —NHCH$_2$CONHCH(COO)CH$_2$CH$_2$COO)

δ 3.4 (s, 3H, —O(CH$_2$CH$_2$O)$_7$CH$_3$)
δ 3.5–3.9 (b, 30H, —OCH$_2$CH$_2$O(CH$_2$CH$_2$O)$_6$CH$_3$, —NHCH$_2$CONHCH(COO)CH$_2$CH$_2$COO)
δ 4.0–4.4 (b, 4H, —OCH$_2$CH$_2$O(CH$_2$CH$_2$O)$_6$CH$_3$, —NHCH$_2$CONHCH(COO)CH$_2$CH$_2$COO)
$^{31}$P-NMR spectra (D$_2$O, ppm): δ 21.8, 18.1

Molecular Weight (Mw): 24,193

Example 4

Preparation of pol{[methoxy poly(ethylene glycol) 350][glycylglutamato-trans-(±)-1,2-diaminocyclohexaneplatinum(II)]phosphazene}, {NP(MPEG350)$_{1.2}$[(GlyGlu)Pt(dach)]$_{0.8}$}$_n$ According to the same method as described in Example 1, the desired product of the title polyphosphazene-platinum (II) conjugate was prepared by using methoxy poly(ethylene glycol) having molecular weight of 350 (7.25 g, 20.7 mmol), a piece of sodium metal (1.0 g, 25 mmol), poly (dichlorophosphazene) (5% AlCl$_3$, 2.00 g, 17.2 mmol), triethylamine (18.86 g, 186.3 mmol), glycylglutamic acid ethyl ester (6.15 g, 20.7 mmol), Ba(OH)$_2$.8H$_2$O (0.79 g, 2.5 mmol) and Pt(dach)SO$_4$ (1.1 g, 2.5 mmol) in 76% yield.

Composition: $C_{28}H_{54}N_5O_{14}PPt.3H_2O$

Elemental analysis data: C(36.45), H(6.36), N(6.68), Pt(13.7)

Theoretical Value: C(37.16), H(6.93), N(7.78), Pt(17.01)

H-NMR spectra (D$_2$O, ppm):

δ 0.9–1.3 (b, 4H, —NH$_2$CHCH$_2$CH$_2$CH$_2$CH$_2$CHNH$_2$)

δ 1.3–1.5 (b, 2H, —NH$_2$CHCH$_2$CH$_2$CH$_2$CH$_2$CHNH$_2$)

δ 1.6–2.0 (b, 4H, —NH$_2$CHCH$_2$CH$_2$CH$_2$CH$_2$CHNH$_2$, —NHCH$_2$CONHCH(COO)CH$_2$CH$_2$COO)

δ 2.0–2.3 (b, 4H, —NH$_2$CHCH$_2$CH$_2$CH$_2$CH$_2$CHNH$_2$, —NHCH$_2$CONHCH(COO)CH$_2$CH$_2$COO)

δ 3.4 (s, 3H, —O(CH$_2$CH$_2$O)$_7$CH$_3$)
δ 3.5–3.9 (b, 30H, —OCH$_2$CH$_2$O(CH$_2$CH$_2$O)$_6$CH$_3$, —NHCH$_2$CONHCH(COO)CH$_2$CH$_2$COO)
δ 4.0–4.4 (b, 4H, —OCH$_2$CH$_2$O(CH$_2$CH$_2$O)$_6$CH$_3$, —NHCH$_2$CONHCH(COO)CH$_2$CH$_2$COO)
$^{31}$P-NMR spectra (D$_2$O, ppm): δ 22.3, 18.3

Molecular Weight: 66,584

Example 5

Preparation of poly{[methoxy poly(ethylene glycol) 350][glycylglutamato-trans-(±)-1,2-diaminocyclohexaneplatinum(II)]phosphazene}, {NP(MPEG350)$_{1.4}$[(GlyGlu)Pt(dach)]$_{0.6}$}$_n$ According to the same method as described in Example 1, the desired product of the title polyphosphazene-platinum (II) conjugate was prepared by using methoxy poly(ethylene glycol) having molecular weight of 350 (7.25 g, 20.7 mmol), a piece of sodium metal (10 g, 25 mmol), poly (dichlorophosphazene) (5% AlCl$_3$, 2.00 g, 17.2 mmol), triethylamine (18.86 g, 186.3 mmol), glycylglutamic acid ethyl ester (6.10 g, 20.7 mmol), Ba(OH)$_2$.8H$_2$O(0.7 g, 2.2 mmol) and Pt(dach)SO$_4$(0.89 g, 2.2 mmol) in 69% yield.

Composition: C$_{29}$H$_{57}$N$_5$O$_{13}$PPt.6H$_2$O

Elemental analysis data: C(35.66), H(6.18), N(5.66), Pt(10.6)

Theoretical Value: C(36.39), H(7.08), N(6.09), Pt(12.32)

H-NMR spectra (D$_2$O, ppm):

δ 0.9–1.3 (b, 4H, —NH$_2$CHCH$_2$CH$_2$CH$_2$CH$_2$CHNH$_2$)

δ 1.3–1.5 (b, 2H, —NH$_2$CHCH$_2$CH$_2$CH$_2$CH$_2$CHNH$_2$)

δ 1.6–2.0 (b, 4H, —NH$_2$CHCH$_2$CH$_2$CH$_2$CH$_2$CHNH$_2$, —NHCH$_2$CONHCH(COO)CH$_2$CH$_2$COO)

δ 2.0–2.3 (b, 4H, —NH$_2$CHCH$_2$CH$_2$CH$_2$CH$_2$CHNH$_2$, —NHCH$_2$CONHCH(COO)CH$_2$CH$_2$COO)

δ 3.4 (s, 3H, —O(CH$_2$CH$_2$O)$_7$CH$_3$)
δ 3.5–3.9 (b, 30H, —OCH$_2$CH$_2$O(CH$_2$CH$_2$O)$_6$CH$_3$, —NHCH$_2$CONHCH(COO)CH$_2$CH$_2$COO)
δ 4.0–4.4 (b, 4H, —OCH$_2$CH$_2$O(CH$_2$CH$_2$O)$_6$CH$_3$, —NHCH$_2$CONHCH(COO)CH$_2$CH$_2$COO)
$^{31}$P-NMR spectra (D$_2$O, ppm): δ 22.0, 18.9
Molecular Weight: 46,527

Example 6

Preparation of poly{[methoxy poly(ethylene glycol) 350][glycylglutamato-trans-(±)-1,2-diaminocyclohexaneplatinum(II)]phosphazene}, {NP(MPEG350)$_{1.12}$[(GlyGlu)Pt(dach)]$_{0.88}$}$_n$ According to the same method as described in Example 1, the desired product of the title polyphosphazene-platinum (II) conjugate was prepared by using methoxy poly(ethylene glycol) having molecular weight of 350 (6.78 g, 19.3 mmol), a piece of sodium metal (0.57 g, 24.8 mmol), poly (dichlorophosphazene) (3% AlCl$_3$, 2.00 g, 17.2 mmol), triethylamine (18.86 g, 186.3 mmol), glycylglutamic acid ethyl ester (9.0 g, 29.0 mmol), Ba(OH)$_2$.8H$_2$O (0.63 g, 2.0 mmol) and Pt(dach)SO$_4$ (0.81 g, 2.0 mmol) in 70% yield.

Composition: C$_{28}$H$_{54}$N$_5$O$_{13}$PPt

Elemental analysis data: C(39.46), H(6.56), N(7.06)

Theoretical Value: C(39.56), H(6.45), N(6.83)

H-NMR spectra (D$_2$O, ppm):

δ 0.9–1.3 (b, 4H, —NH$_2$CHCH$_2$CH$_2$CH$_2$CH$_2$CHNH$_2$)

δ 1.3–1.5 (b, 2H, —NH$_2$CHCH$_2$CH$_2$CH$_2$CH$_2$CHNH$_2$)

δ 1.6–2.0 (b, 4H, —NH$_2$CHCH$_2$CH$_2$CH$_2$CH$_2$CHNH$_2$, —NHCH$_2$CONHCH(COO)CH$_2$CH$_2$COO)

δ 2.0–2.3 (b, 4H, —NH$_2$CHCH$_2$CH$_2$CH$_2$CH$_2$CHNH$_2$, —NHCH$_2$CONHCH(COO)CH$_2$CH$_2$COO)

δ 3.4 (s, 3H, —O(CH$_2$CH$_2$O)$_7$CH$_3$)
δ 3.5–3.9 (b, 30H, —OCH$_2$CH$_2$O(CH$_2$CH$_2$O)$_6$CH$_3$, —NHCH$_2$CONHCH(COO)CH$_2$CH$_2$COO)
δ 4.0–4.4 (b, 4H, —OCH$_2$CH$_2$O(CH$_2$CH$_2$O)$_6$CH$_3$, —NHCH$_2$CONHCH(COO)CH$_2$CH$_2$COO)
$^{31}$P-NMR spectra (D$_2$O, ppm): δ 23.0, 18.9
Molecular Weight (Mw): 78,119

Example 7

Preparation of poly{[methoxy poly(ethylene glycol) 550][glycylglutamato-trans(±trans-(±)-1,2-diaminocyclohexaneplatinum(II)]phosphazene}, {NP(MPEG350)$_{1.12}$[(GlyGlu)Pt(dach)]$_{0.88}$}$_n$ According to the same method as described in Example 1, the desired product of the title polyphosphazene-platinum (II) conjugate was prepared by using methoxy poly(ethylene glycol) having molecular weight of 550 (6.78 g, 19.3 mmol), a piece of sodium metal (0.9 g, 22.5 mmol), poly (dichlorophosphazene) (3% AlCl$_3$, 2.00 g, 17.3 mmol), triethylamine (18.9 g, 186.3 mmol), glycylglutamic acid ethyl ester (8.4 g, 27.0 mmol), Ba(OH)$_2$.8H$_2$O (0.79 g, 2.5 mmol) and Pt(dach)SO$_4$(1.1 g, 2.5 mmol) in 70% yield.

Composition: C$_{37}$H$_{73}$N$_5$O$_{17}$PPt

Elemental analysis data: C(40.86), H(6.64), N(6.46), Pt(19.25)

Theoretical Value: C(40.17), H(6.64), N(8.33), Pt(19.46)

H-NMR spectra (D$_2$O, ppm):

δ 0.9–1.3 (b, 4H, —NH$_2$CHCH$_2$CH$_2$CH$_2$CH$_2$CHNH$_2$)

δ 1.3–1.5 (b, 2H, —NH$_2$CHCH$_2$CH$_2$CH$_2$CH$_2$CHNH$_2$)

δ 1.6–2.0 (b, 4H, —NH$_2$CHCH$_2$CH$_2$CH$_2$CH$_2$CHNH$_2$, —NHCH$_2$CONHCH(COO)CH$_2$CH$_2$COO)

δ 2.0–2.3 (b, 4H, —NH$_2$CHCH$_2$CH$_2$CH$_2$CH$_2$CHNH$_2$, —NHCH$_2$CONHCH(COO)CH$_2$CH$_2$COO)

δ 3.4 (s, 3H, —O(CH$_2$CH$_2$O)$_7$CH$_3$)
δ 3.5–3.9 (b, 30H, —OCH$_2$CH$_2$O(CH$_2$CH$_2$O)$_6$CH$_3$, —HCH$_2$CONHCH(COO)CH$_2$CH$_2$COO)
δ 4.0–4.4 (b, 4H, —OCH$_2$CH$_2$O(CH$_2$CH$_2$O)$_6$CH$_3$, —NHCH$_2$CONHCH(COO)CH$_2$CH$_2$COO)
$^{31}$P-NMR spectra (D$_2$O, ppm): δ 22.3, 18.4

Molecular Weight (Mw): 88,304

Example 8

Preparation of poly{[methoxy poly(ethylene glycol) 350][glycylaspartato-trans-(±)-1,2-diaminocyclohexaneplatinum(II)]phosphazene}, {NP(MPEG350)$_{1.1}$[(GlyAsp)Pt(dach)]$_{0.9}$}$_n$ According to the same method as described in Example 1, the desired product of the title polyphosphazene-platinum (II) conjugate was prepared by using methoxy poly(ethylene glycol) having molecular weight of 350 (5.70 g, 19.0 mmol), a piece of sodium metal (1.0 g, 25 mmol), poly (dichlorophosphazene) (3% AlCl$_3$, 2 g, 17.2 mmol), triethylamine (18.9 g, 186.3 mmol), glycylaspartic acid ethyl ester (6.10 g, 20.7 mmol), Ba(OH)$_2$.8H$_2$O (0.79 g, 2.5 mmol) and Pt(dach)SO$_4$ (1.1 g, 2.5 mmol) in 70% yield.

Composition: C$_{28}$H$_{55}$N$_5$O$_{13}$PPt.6H$_2$O

Elemental analysis data: C(32.79), H(5.22), N(6.48)

Theoretical Value: C(33.31), H(6.56), N(7.35), Pt(20.04)

H-NMR spectra (D$_2$O, ppm):

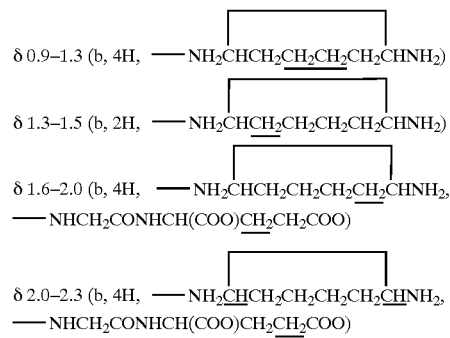

δ 3.4 (s, 3H, —O(CH$_2$CH$_2$O)$_7$CH$_3$)
δ 3.5–3.9 (b, 30H, —OCH$_2$CH$_2$O(CH$_2$CH$_2$O)$_6$CH$_3$, —NHCH$_2$CONHCH(COO)CH$_2$CH$_2$COO)
δ 4.0–4.4 (b, 4H, —OCH$_2$CH$_2$O(CH$_2$CH$_2$O)$_6$CH$_3$, —NHCH$_2$CONHCH(COO)CH$_2$CH$_2$COO)
$^{31}$P-NMR spectra (D$_2$O, ppm): δ 22.5, 18.5

Molecular Weight (Mw): 171,230

Example 9

Preparation of poly{[methoxy poly(ethylene glycol) 350][glycylamino-malonatotrans(±)-1,2-diaminocyclohexaneplatinum(II)]phosphazene}, {NP(MPEG350)$_{1.0}$[(GlyMal)Pt(dach)]$_{1.0}$}$_n$ According to the same method as described in Example 1, the desired product of the title polyphosphazene-platinum (II) conjugate was prepared by using methoxy poly(ethylene glycol) having molecular weight of 350 (6.35 g, 17.3 mmol), a piece of sodium metal (1.0 g, 25 mmol), poly (dichlorophosphazene) (10% AlCl$_3$, 2.00 g, 17.2 mmol), triethylamine (18.86 g, 186.3 mmol), diethylaminomalonic acid (4.2 g, 20.8 mmol), Ba(OH)$_2$.8H$_2$O (0.79 g, 2.5 mmol) and Pt(dach)SO$_4$(1.1 g, 2.5 mmol) in 78.0% yield.

Composition: C$_{29}$H$_{55}$N$_5$O$_{13}$PPt

Elemental analysis data: C(37.58), H(6.08), N(7.83), Pt(21.1)

Theoretical Value: C(38.37), H(6.11), N(7.71), Pt(21.49)

H-NMR spectra (D$_2$O, ppm):

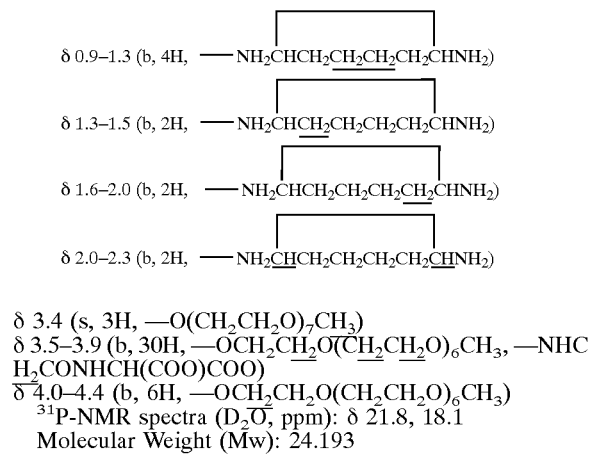

δ 3.4 (s, 3H, —O(CH$_2$CH$_2$O)$_7$CH$_3$)
δ 3.5–3.9 (b, 30H, —OCH$_2$CH$_2$O(CH$_2$CH$_2$O)$_6$CH$_3$, —NHCH$_2$CONHCH(COO)COO)
δ 4.0–4.4 (b, 6H, —OCH$_2$CH$_2$O(CH$_2$CH$_2$O)$_6$CH$_3$)
$^{31}$P-NMR spectra (D$_2$O, ppm): δ 21.8, 18.1

Molecular Weight (Mw): 24.193

Example 10

Preparation of poly{[methoxy poly(ethylene glycol) 750][glycylglutamato-trans-(±)-1,2-diaminocyclohexaneplatinum(II)]phosphazene}, {NP(MPEG750)$_{1.0}$[(GlyGlu)Pt(dach)]$_{1.0}$}$_n$ According to the same method as described in Example 1, the desired product of the title polyphosphazene-platinum (II) conjugate was prepared by using methoxy poly(ethylene glycol) having molecular weight of 750 (12.95 g, 17.3 mmol), a piece of sodium metal (0.8 g, 20 mmol), poly (dichlorophosphazene) (10% AlCl$_3$, 2.00 g, 17.2 mmol), triethylamine (18.86 g, 186.3 mmol), glycylglutamic acid ethyl ester (7.63 g, 25.9 mmol), Ba(OH)$_2$.8H$_2$O (0.95 g, 3.0 mmol) and Pt(dach)SO$_4$ (1.21 g, 3.0 mmol)in 70% yield.

Composition: C$_{46}$H$_{90}$N$_5$O$_{22}$PPt.6H$_2$O

Elemental analysis data: C(39.781), H(6.66), N(5.61)

Theoretical Value: C(40.73), H(7.21), N(6.1), Pt(15.46)

H-NMR spectra (D$_2$O, ppm):

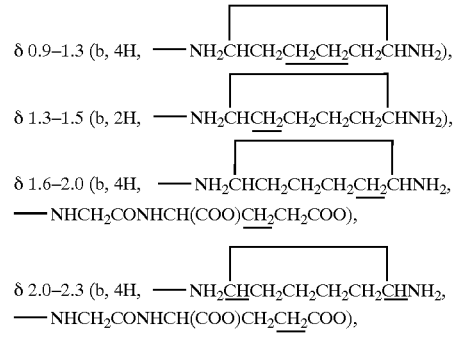

δ 3.4 (s, 3H, —O(CH$_2$CH$_2$O)$_7$CH$_3$),
δ 3.5–3.9 (b, 63H, —OCH$_2$CH$_2$O(CH$_2$CH$_2$O)$_6$CH$_3$, —NHCH$_2$CONHCH(COO)CH$_2$CH$_2$COO),
δ 4.0–4.4 (b, 4H, —OCH$_2$CH$_2$O(CH$_2$CH$_2$O)$_6$CH$_3$, —NHCH$_2$CONHCH(COO)CH$_2$CH$_2$COO)
$^{31}$P-NMR spectra (D$_2$O, ppm): δ 22.3, 19.2

Molecular Weight (Mw): 33,433

Example 11

Preparation of poly{[methoxy poly(ethylene glycol) 350][glycylglutamato-(2,2-dimethyl-1,3-propanediamine)platinum(II)]phosphazene}, {NP(MPEG350)$_{1.0}$[(GlyGlu)Pt(dmpda)]$_{1.0}$}$_n$ According to the same method as described in Example 1, the desired product of the title polyphosphazene-platinum (II) conjugate was prepared by using methoxy poly(ethylene glycol) having molecular weight of 350 (5.01 g, 14.30 mmol), a piece of sodium metal (0.8 g, 20 mmol), poly (dichlorophosphazene) (5% $AlCl_3$, 2.00 g, 17.2 mmol), triethylamine (18.9 g, 186.3 mmol), glycylglutamic acid ethyl ester (7.6 g, 25.9 mmol), $Ba(OH)_2 \cdot 8H_2O$ (0.63 g, 2.0 mmol) and platinum(II) sulfate of 2,2-dimethyl-1,3-propanediamine (dmpda) $((dmpda)PtSO_4$, 0.81 g, 2.0 mmol) in 70% yield.

Composition: $C_{28}H_{54}N_5O_{14}PPt \cdot 4H_2O$

Elemental analysis data: C(35.41), H(5.352), N(7.831)

Theoretical Value: C(35.46), H(6.80), N(7.64)

H-NMR spectra ($D_2O$, ppm):

δ 0.9 (b, 6H, —$NH_2CH_2CCH_3CH_3CH_2NH_2$),

δ 1.6–2.0 (b, 2H, —$NHCH_2CONHCH(COO)CH_2CH_2COO$),

δ 2.0–2.3 (b, 4H, —$NHCH_2CONHCH(COO)CH_2CH_2COO$),

δ 2.2 (b, 2H, —$NH_2CH_2CCH_3CH_3CH_2NH_2$),

δ 3.4 (s, 3H, —$O(CH_2CH_2O)_7CH_3$),

δ 3.5–3.9 (b, 30H, —$OCH_2CH_2O(CH_2CH_2O)_6CH_3$, —$NHCH_2CONHCH(COO)CH_2CH_2COO$),

δ 4.0–4.4 (b, 4H, —$OCH_2CH_2O(CH_2CH_2O)_6CH_3$, —$NHCH_2CONHCH(COO)CH_2CH_2COO$)

$^{31}$P-NMR spectra ($D_2O$, ppm): δ 22.4, 18.4

Molecular Weight (Mw): 32,559

Example 12

Preparation of poly{[methoxy poly(ethylene glycol) 350][glycylglutamato-ethylenediamineplatinum(II)] phosphazene}, $\{NP(MPEG350)_{1.0}, [(GlyGlu)Pt(en)]_{1.0}\}_n$ According to to the same method as described in Example 1, the desired product of the title polyphosphazene-platinum (II) conjugate was prepared by using methoxy poly(ethylene glycol) having molecular weight of 350 (5.01 g, 14.3 mmol), a piece of sodium metal (0.8 g, 20 mmol), poly (dichlorophosphazene) (5% $AlCl_3$, 2.00 g, 17.2 mmol), triethylamine (18.9 g, 186.3 mmol), glycylglutamic acid ethyl ester (7.6 g, 25.9 mmol), $Ba(OH)_2 \cdot 8H_2O$ (0.92 g, 2.9 mmol) and platinum(II) sulfate of ethylenediamine (en) $(Pt(en)SO_4$, 1.13 g, 2.9 mmol) in 70% yield.

Composition: $C_{25}H_{54}N_4O_{13}PPt \cdot 4H_2O$

Elemental analysis data: C(33.41), H(5.35), N(7.831)

Theoretical Value: C(33.92), H(6.953), N(7.88)

H-NMR spectra ($D_2O$, ppm):

δ 1.8–2.1 (b, 2H, —$NHCH_2CONHCH(COO)CH_2CH_2COO$),

δ 2.1–2.6 (b, 4H, —$NH_2CH_2CH_2NH_2$),

δ 2.6–2.7 (b, 4H, —$NHCH_2CONHCH(COO)CH_2CH_3CH_2CH_2COO$),

δ 3.4 (s, 3H, —$O(CH_2CH_2O)_7CH_3$),

δ 3.5–3.9 (b, 30H, —$OCH_2CH_2O(CH_2CH_2O)_6CH_3$, —$NHCH_2CONHCH(COO)CH_2CH_2COO$),

δ 4.0–4.4 (b, 4H, —$OCH_2CH_2O(CH_2CH_2O)_6CH_3$, —$NHCH_2CONHCH(COO)CH_2CH_2COO$)

$^{31}$P-NMR spectra ($D_2O$, ppm): δ 22.4, 18.4

Molecular Weight (Mw): 18,182

Example 13

Assay for Enhanced Permeability and Retention Effect of the polyphosphazene-platinum(II) Conjugates Male C57 BL/6N mice (8–9 weeks old, 25–27 g) were adopted for 4 days in the dark and light at intervals of 12 hr, and then inoculated subcutaneously with the B16F10 melanoma cells ($1 \times 10^6$ cells suspended in PBS) in the back region. After 2 weeks, when the tumor was grown up to 10 mm in diameter, the drugs dissolved in saline (20 mg/kg) were injected in a tail vein. The animals were sacrificed at 2 hrs and 24 hrs after drug administration. Blood samples were collected by heart puncture with a syringe. Tumor and muscle (normal tissue) were removed from animals, and stored at −80° C. for analysis. The analysis of the drugs in the biological samples was based on the measurement of the Pt(II). After the samples were treated with $c$-$H_2SO_4$, $c$-$HNO_3$ and finally aqua regia, platinum content was measured by ICP-MS (Model ELAN5000, Perkin Elmer, Norwalk, Conn.).

Table 1 shows TTR (tumor tissue/normal tissue distribution) values. It can be seen from Table 1 that the best tumor selectivity was achieved when the molecular weight of the polyphosphazene-platinum(II) conjugate was in the range of 80,000–100,000.

TABLE 1

| | | TTR values (tumor tissue/normal tissue distribution) | |
|---|---|---|---|
| Compound | Molecular Weight | 2 hours | 24 hours |
| Example 1 | ~100,000 | 2.8 | 5.2 |
| Example 2 | ~36,200 | 4.8 | 3.6 |
| Example 4 | ~66,600 | 2.5 | 4.0 |
| Example 7 | ~88,300 | 3.8 | 7.4 |

Example 14

Assay for the Antitumor Activity of the polyphosphazene-platinum(II) Conjugates Against the Leukemia L1210 Cell Line Antitumor activities for the polyphosphazene-platinum (II) conjugates according to the present invention against leukemia L1210 cell line were assayed according to a known method (S. S. Lee, O.-S. Jung, C. O. Lee, S. U. Choi, M.-J. Jun and Y. S. Sohn, *Inorg. Chim. Acta*, 239, 133(1995)), and the results are shown in Table 2.

TABLE 2

| Compound | In vitro ($ID_{50}$, μM) | in vivo (T/C (%)/dosage (mg/kg)) |
|---|---|---|
| Example 1 | 8.2 | 178/30 |
| Example 2 | 6.9 | >305.6/60, 208.1/30 |
| Example 3 | 3.4 | toxic/60, 194.1/30 |
| Example 4 | 3.5 | 216.8/60, 186.8/30 |
| Example 5 | 6.2 | 231.1/60, 244.3/30 |
| Example 7 | >40 | 209.4/60, 228.2/30 |

Example 15

In vivo Xenograft Tests for the polyphosphazene-platinum(II) Conjugate Against a Gastric Tumor Cell Line (YCC-3)

The in vivo sensitivity of the present conjugate drug against a gastric tumor cell line (YCC-3) was assayed using nu/nu mice (6–8 weeks old, 20–25 g). After being treated with 0.25% Trypsin-EDTA, the cultivated tumor cells were centrifuged in PBS solution for 5 minutes. This process was repeated three or more times, and then the tumor cells were made into a single floated tumor cell. The concentration of the tumor cells in PBS solution was calculated from the number of cells measured by a hemocytometer. The tumor cells were then kept in ice and were injected into mice within 30 minutes. The single floated tumor cells (4×10$^7$) in 100 μl of PBS solution were subcutaneously injected into the right side of each mouse using an 1 ml syringe.

When the tumor was grown up to reach 0.5 cm$^3$ in size, the testing drugs were administered by an intraperitoneal injection in two dosages (60 mg/kg and 30 mg/kg) in 100 μl of PBS solution. In the case of the control group, only the same amount of PBS solution was injected. Weights of the mice and tumor size were measured every two days. Size of the tumor was calculated with an equation of length×width×width/2.

The results are shown in Table 3. It can be seen from the table that the tumor tissue growth rate in the case of the conventional cisplatin is not significantly different from that of the control group, whereas in the case of the compound of Example 3 according to the present invention, its inhibition effect on the tumor tissue growth rate was outstanding compared with that of cisplatin after 60 days from the injection of the testing drug. Therefore, it was discovered that antitumor activity of the compound according the present invention is superior to that of the conventional antitumor agent.

TABLE 3

| | | The tumor tissue size (mm$^3$) after injection of an antitumor agent | | | |
|---|---|---|---|---|---|
| Compound | Dosage (mg/kg) | 18 days | 32 days | 48 days | 60 days |
| Control Group | 0 | 169.43 | 400.16 | 712.96 | 806.62 |
| Cisplatin | 4 | 161.36 | 330.62 | 588.02 | 815.79 |
| Example 3 | 30 | 121.92 | 210.38 | 111.23 | 22.71 |
| Example 3 | 60 | 32.69 | 72.08 | 65.36 | 91.10 |

As described above, a polyphosphazene-platinum(II) conjugate having good tumor selectivity and anticancer activity according to the present invention has been provided. The polyphosphazene-platinum(II) conjugate according to the present invention shows high tumor selectivity, and therefore, it may be used widely as a new antitumor agent with high response rate and low adverse effects.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A polyphosphazene-platinum(II) conjugate represented by the following chemical formula (1).

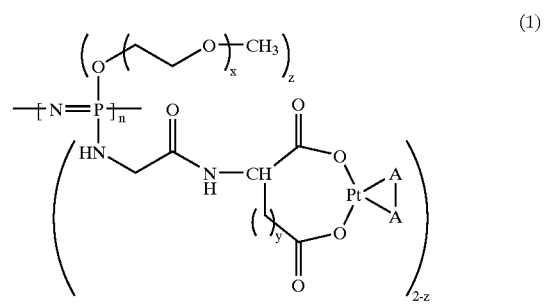

wherein x represents the number of the ethylene oxide repeating unit and is 7, 12 or 16; y is 0, 1 or 2; z represents molar content of polyethylene glycol in the range of 0.5–1.5; n represents degree of polymerization of polyphosphazene in the range of 30–100; and A-A represents a diamine.

2. The polyphosphazene-platinum(II) conjugate according to claim 1, which has a hydrodynamic volume in a diameter of 10–100 nm in aqueous solution and shows tumor tissue selectivity.

3. The polyphosphazene-platinum(II) conjugate according to claim 1, wherein the diamine is selected from the group consisting of trans(±)-1,2-diaminocyclohexane, 2,2-dimethyl-1,3-propanediamine and ethylenediamine.

4. A preparation method of a polyphosphazene-platinum (II) conjugate represented by chemical formula (1), comprising the steps of:

(a) reacting a poly(dichlorophosphazene) of chemical formula (3) sequentially with a sodium salt of methoxy poly(ethylene glycol) of chemical formula (5) and a dipeptide ethyl ester of chemical formula (6), to obtain a polyphosphazene derivative of chemical formula (7);

(b) hydrolyzing the ester group present in the polyphosphazene derivative of chemical formula (7) using an alkali in an alcohol solution, to obtain a hydrolysate of the polyphosphazene derivative of chemical formula (7) and (c) reacting the hydrolysate obtained in step (b) with a platinum(II) complex of chemical formula (8), to obtain the polyphosphazene-platinum(II) conjugate of chemical formula (1):

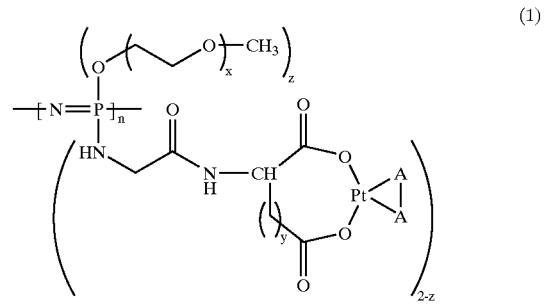

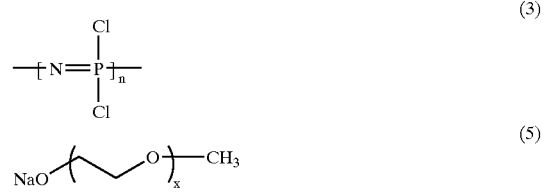

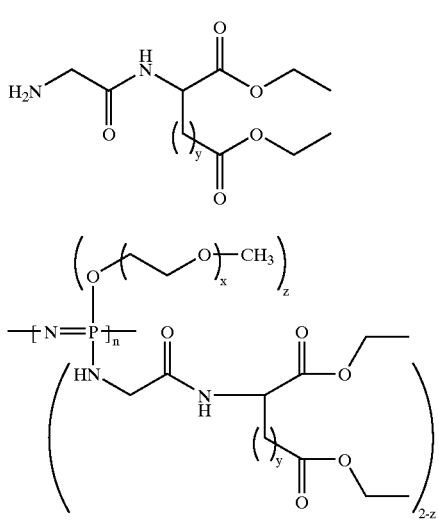

(A-A)PtL (8)

wherein x represents the number of the ethylene oxide repeating unit and is 7, 12 or 16; y is 0, 1 or 2; z represents molar content of polyethylene glycol in the range of 0.5–1.5; n represents degree of polymerization of polyphosphazene in the range of 30–100; A-A represents a diamine; and L represents one or two anionic ligand.

5. The preparation method according to claim 4, wherein the alkali is barium hydroxide or sodium hydroxide.

6. The preparation method according to claim 4, wherein the anionic ligand is sulfate or nitrate.

7. The preparation method according to claim 6, wherein the diamine is selected from the group consisting of trans (±)-1,2-diaminocyclohexane, 2,2-dimethyl-1,3-propanediamine and ethylenediamine.

8. The preparation method according to claim 4, wherein molecular weight of methoxy poly(ethylene glycol) is 350, 550 or 750.

9. The preparation method according to claim 4, wherein the dipeptide ethyl ester of chemical formula (6) is selected from the group consisting of glycylglutamate, glycylaspartate and glycylaminomalonate.

10. The preparation method according to claim 5, wherein the steps (b) and (c) comprise hydrolyzing ester group present in the polyphosphazene derivative of chemical formula (7) with barium hydroxide; reacting hydrolysate with (diamine)platinum(II) complex of chemical formula (8) in which L is sulfate; and removing precipitate of barium sulfate by filtering.

* * * * *